United States Patent [19]

Collier et al.

[11] Patent Number: 5,059,586

[45] Date of Patent: Oct. 22, 1991

[54] METHOD FOR ENHANCING GROWTH OF MAMMARY PARENCHYMA

[75] Inventors: Robert J. Collier, University City; Michael F. McGrath, Chesterfield, both of Mo.

[73] Assignee: Monsanto Company, St. Louis, Mo.

[21] Appl. No.: 92,009

[22] Filed: Sep. 2, 1987

Related U.S. Application Data

[63] Continuation-in-part of Ser. No. 837,477, Mar. 7, 1986, abandoned.

[51] Int. Cl.$^5$ ...................... A61K 37/24; A61K 37/36
[52] U.S. Cl. ........................................ 514/12; 514/21; 514/2; 424/105
[58] Field of Search .................... 424/105; 514/12, 21

[56] References Cited

U.S. PATENT DOCUMENTS 4,011,312  3/1977  Reuter'et al. .......................... 424/78
4,521,409  6/1985  Bauman et al. ........................ 514/21

OTHER PUBLICATIONS

Peel, J. Nutr., 111, 1662-1671 (1981).
Bauman, Commonwealth Agricultural Bureau, Abst. No. 85009653 (1984).
Michael, Chem. Abst., 102, 56(1985), Abst. No. 160488t.
Merriam-Webster Dictionary, 3rd. New International Dictionary, G & C Merriam Co., Springfield, Mass., 1967, p. 434.
R. Akers et al. (1981) Endocrinology 109:23–30 "Prolactin Regulation of Milk Secretion and Biochemical Differentation of Mammary Epithelial Cells in Periparturient Cows".
R. Akers (1985) J. Dairy Sci. 68:501-519, "Lactogenic Hormones: Binding Sites, Mammary Growth, Secretory Cell Differentiation and Milk Biosynthesis in Ruminants".
C. W. Welsch et al. (1979), Cancer Research 39:2046-2050 Hormone–Induced Growth and Lactogenesis of Grafts of Bovine Mammary Gland Maintained in the Athymic "Nude" Mouse.
Imagawa, W., et al., "Serum-Free Growth of Normal and Tumor Mouse Mammary Epithelial Cells in Primary Culture", 79 Proc. Natl. Acad. Sci. U.S.A. 4074–77 (1982).
Taketani, Y., et al., "Epidermal Growth Factor Stimulates Cell Proliferation and Inhibits Functional Differentiation of Mouse Mammary Epithelial Cells in Culture", 113(3) Endocrin. 871-77 (1983).
Taketani, Y. et al., "Biological Action of Epidermal Growth Factor and its Functional Receptors in Normal Mammary Epithelial Cells", 80 Proc. Natl. Acad. Sci, U.S.A. 2647-50 (1983).
Tonnelli, Q. J. et al., "Epidermal Growth Factor Requirement for Development of Cultured Mammary Gland", 285 Nature 250-52 (1980).
Turkington, R. W., "The Role of Epithelial Growth Factor in Mammary Gl and Development in Vitro", 57 Exper. Cell Res. 79-85 (1969).
Yang, J. et al., "Growth Factor–and Cyclic Nucleotide–Induced Proliferation of Normal and Malignant Mammary Epithelial Cells in Primary Culture".
Pasco, D., et al., "Effect of Hormones and EGF on Proliferation of Rat Mammary Epithelium Enriched for Alveoli", 141 Exper. Cell Res. 313-24 (1982).
McGrath, M. et al., "Differential Response of Normal Rat Mammary Epithelial Cells to Mammogenic Hormones and EGF", 125 J. Cell Physiology 182–91 (1985).
Kidwell, W. R. et al., "Purification of a Mammary-Derived Growth Pactor from Human Milk and Human Mammary Tumors", 260(9) J. Biol. Chem. 5745-52 (May 10, 1985).
Lyons, W. R., "The Direct Mammotrophic Action of Lactogenic Hormone", 51 Proc. Soc. Exptl. Biol. Med. 308-311 (1942).
Fiddler et al., "Effects of Intraductal Prolactin on Some Aspects of the Ultrastructure and Biochemistry of Mammary Tissue in the Pseudopregnant Rabbit", 49 J. Endocrin. 459-69 (1971).
Bradley et al., "The Response of Rabbit Mammary Glands to Locally Administered Prolactin", 14 J. Endocrin. 28-36 (1956).
Meites et al., "The Introduction of Lactation During Pregnancy in Rabbits and the Specificity of the Lactogenic Hormone", 150 Amer. J. Physiol., 394-99 (1947).
Spinelli, J. S. et al., "Drugs in Veterinary Practice", C. V. Mosby Co., St. Louis, Mo. (1978).
Lyons et al., "The Hormonal Control of Mammary Growth and Lactation", 14 Recent Prog. Hormone Res. 219-54 (1958).
Daniel et al., "Reinitiation of Growth in Senescent Mouse Mammary Epithelium in Response to Cholera Toxin", 224 Sci. 1245-47 (1984).
Siberstein et al., "In Vivo, cAMP Stimulantes Growth and Morphogenesis of Mouse Mammary Ducts", 81 Proc. Natl. Acad. Sci. U.S.A. 4950-54 (1984).

Primary Examiner—F. T. Moezie
Attorney, Agent, or Firm—Carol H. Clayman; George R. Beck

[57] ABSTRACT

The growth of milk-producing mammary parenchyma in a mammal can be significantly enhanced by administering to the mammal by intramammary infusion a substance having a mitogenic effect on mammary epithelial cells in said mammal. Good growth enhancement can be achieved using very small quantities of such substances, and in relatively short periods of time.

19 Claims, No Drawings

METHOD FOR ENHANCING GROWTH OF MAMMARY PARENCHYMA

CROSS-REFERENCE TO RELATED APPLICATION

This is a continuation-in-part of copending application Ser. No. 837,477 filed Mar. 7, 1986, now abandoned.

BACKGROUND OF THE INVENTION

Milk production by a mammal is ultimately limited by the amount of mammary parenchyma (secretory tissue) in the mammary gland. Typically, milk yield has been found to be highly correlated with parenchyma wet weight, dry weight, dry fat-free weight and total gland DNA. In 43 Proc. N.Z. Soc. Anim. Prod. 71 (1983), Davis et al attributed increased milk production in genetically superior animals entirely to increased udder volume which is also related to the quantity of parenchyma cells.

Classical evidence indicates that mammary parenchyma growth is directed by pituitary, ovarian, adrenal, placental or locally-derived tissue factors. See Cowie, 15 Mono-graphs on Endocrinology (1980) and U.S. Pat. No. 4,521,409 issued June 4, 1985 to Bauman and Sejrsen, in which it is disclosed that growth of mammary parenchyma in a ruminant can be increased by administering a growth hormone (somatotropin) into the ruminant's blood stream between about the onset of puberty and about the first parturition (preferably about the first conception).

If administered into an animal's blood stream, most mitogens for mammary parenchyma cells bind additionally to receptors in many of the animal's other tissues. Due to such dilution of the desired effect on mammary growth-stimulating receptors, increasing mammary parenchyma via administration into the blood stream would be expected to require relatively large quantities of such mitogens. Hence there is great incentive to develop a practical technique for increasing the milk production capacity and/or efficiency of a mammal that is not dependent on administration into the mammal's blood stream.

Using rabbits, mice and rats that were physiologically abnormal, i.e., ovariectomized and/or pretreated (e.g. with a reproductive hormone) to induce pseudopregnancy, studies have been made of effects on mammary gland development by subcutaneous injection of a somatotropin and/or other hormones, implants that released cholera toxin, or intraductal injection of "lactogenic hormone". Lyons et al, 50 Proc. Soc. Exper. Biol. Med. 308-11 (1942) and 14 Recent Prog. Hormone Res. 219-54 (1958); Fiddler et al, 49 J. Endocrin. 459-69 (1971); Daniel et al, 224 Sci. 1245-47 (1984); and Silberstein et al, 81 Proc. Natl. Acad. Sci. U.S.A. 4950-54 (1984). Based on other studies using rabbits that were pregnant or pretreated (e.g. with a reproductive hormone) to induce pseudo-pregnancy, it has been reported that intraductal injection of prolactin or "lactogenic hormone" induced lactation. Bradley et al, 14 J. Endocrin. 28-36 (1956) and Meites et al, 150 Amer. J. Physiol. 394-99 (1947). Others have studied in vitro effects of mitogens such as an epidermal growth factor, with or without insulin, on the growth of cultured mammary cells of various animal species. Imagawa et al, 79 Proc. Natl. Acad. Sci. U.S.A. 4074-77 (1982); Taketani et al, 113(3) Endocrin. 871 (1983) and 80 Proc. Natl. Acad. Sci. U.S.A. 2647-50 (1983); Tonelli et al, 285 Nature 250-52 (1980); and Turkington, 57 Exper. Cell Res. 79-85 (1969). The disclosures cited in this paragraph are incorporated here by reference.

OBJECTIVES OF THE INVENTION

It is an object of this invention to provide a method which enhances the growth of mammary parenchyma in a female mammal, and thereby significantly increases the milk production capacity and/or efficiency of such a mammal. Another object is such a method having a high degree of specificity in the mammal for the desired increase in parenchyma. Another object is a method requiring use of a small (preferably minimal or near-minimal) quantity of a substance effecting such an enhancement in parenchyma growth. Another object is such a method which can be carried out conveniently. Another object is a method that provides predictably uniform growth-enhancement effects on treated mammary glands in the animal. Another object is a method having little potential for biological side effects in the animal. Other objects are various compositions suitable for convenient and commercially practical use in such methods. These and other objects of the invention will be more fully apparent from the following detailed disclosure.

SUMMARY OF THE INVENTION

We have discovered that these objectives can be achieved in female mammals by intramammary infusion of a substance having a mitogenic effect on mammary epithelial cells in that mammal. Surprisingly, substantial enhancement of normal parenchyma growth can be achieved by this method which does not require administration into the animal's blood stream, subcutaneous injection or implantation, but instead utilizes a convenient administration technique of a kind which, in the case of most dairy cows and some other mammals, has been routinely carried out for infusion of antibiotics. Substantial enhancements of parenchyma growth, and consequently milk production capacity of the mammal over those normally observed can be achieved by this invention utilizing only very small quantities of such substances, and in relatively short intervals of time. These discoveries were quite unexpected, largely because there was no prior art known to indicate that such substances would readily pass from the teat cistern of a mammary gland into contact with cells subject to the mitogenic effects needed to substantially enhance growth of the gland.

DESCRIPTION OF THE INVENTION

This invention is useful for any female mammal in which an increase in mammary parenchyma growth is desired. It is especially useful for ruminants, including cattle such as dairy cows, cows bred primarily for beef production, and heifers of dairy and beef cattle breeds. It is useful in all known breeds of dairy cows, e.g. Holstein, Friesien, Brown Swiss, Jersey, Guernsey, Ayrshire, Milking Shorthorn, and crossbreeds thereof, and in all known breeds of beef cows, e.g. Hereford, Angus, Zebu, Charolais, Brangus, Simmental, Chianina, Dutch Belted, Limousin, and crossbreeds thereof. It is also useful in other ruminants, e.g. sheep and goats of all breeds, as well as various non-ruminants, e.g. swine of all breeds. Most commonly, the invention is used for treatment of mammals that are physiologically normal which, for present purposes, means not ovariectomized and not pretreated (e.g. with a reproductive hormone such as estrogen, gonadotrophin or the like) to induce pseudopregnancy or puberty.

As used herein, the term "mammary parenchyma" refers to tissue in a mammary gland (including that commonly called "mammary epithelium") which is instrumental in production of milk by that gland. Typically in the female, mammary gland growth occurs mainly after the onset of puberty. Usually (e.g. in the heifer) most mammary gland growth occurs during the first gestation. Further growth and/or regrowth of the parenchyma occurs during subsequent gestations. Normally, the mitosis (cell division) causing such growth must be accompanied or followed by sufficient differentiation of the new cells that, following parturition, they will contribute to milk production.

To enhance such growth, this invention can be carried out by administering the substance having the desired mitogenic effect to the mammal between about the onset of puberty (including the peripubertal period) and the mammal's first gestation, or during the first or any subsequent gestation. Thus, typically such administration is carried out in a "dry" period, i.e., while the mammal is non-lactating. In pregnant dairy cows and similar mammals, administration during the last trimester before parturition is usually advantageous. The most preferred intervals for such administration depend on various factors, including the particular substance employed to achieve the desired mitogenic effect. Further details useful in identifying such preferred intervals are set forth hereinafter.

The convenient and surprisingly effective administration technique of this invention is most commonly called intramammary infusion. In mammals such as cows, this technique is routinely used to administer antibiotic-containing ointments or other formulations for prevention or control of mastitis. In practice of this invention, the substance having a mitogenic effect usually can be administered by a similar technique or, even more conveniently, by including it (with or without another parenchyma growth stimulant) in a formulation to be infused for mastitis prevention or control, or for any other purpose.

In this technique, a blunt-tip syringe is inserted through the teat orifice and streak canal such that the substance having a mitogenic effect is deposited in the teat cistern. From there, it normally spreads through the teat cistern, gland cistern and ductal system of the mammary gland. This well-known technique is described in "Drugs in Veterinary Practice", pp. 80-83, by Spinelli et al, C. V. Mosby Co., St. Louis, Mo. (1978) and U.S. Pat. No. 4,011,312 issued Mar. 8, 1977 to Reuter et al, both incorporated here by reference. For purposes of this invention, other procedures should be considered equivalents of intramammary infusion to the extent they deposit such a substance in the teat cistern and thereby result in spreading of same through the ductal system and passage therefrom into mammary tissue where it has an enhancing effect on parenchyma growth.

For purposes of this application, "direct" and "paracrine" mitogenic effects are to be understood as effects that do not require, and in most instances do not involve, the infused substance entering the treated animal's blood stream in an amount that raises its concentration therein to a level sufficient to have, through endocrine regulation, a mitogenic effect of the desired magnitude on parenchyma cells in the animal. For a review of paracrine regulation of mammary gland growth, see Oka et al, 15(1) Clinics in Endocrin. and Metab. 79-97 (1986).

This invention can be carried out using any substance having a significant direct or paracrine mitogenic effect on mammary parenchyma in the mammal to be treated. Many important embodiments are carried out using a substance which acts directly on mammary parenchyma cells in the infused gland to increase their rate of normal cell proliferation. In other embodiments, the substance acts directly on nonparenchyma cells within the gland resulting in such cells providing, through a paracrine effect, a locally increased amount of a substance having a direct mitogenic effect on mammary parenchyma cells in the infused gland.

In some instances, as can be seen from Examples 14-16 hereinafter, intramammary infusion of such a substance results in substantial growth of mammary glands adjacent to those infused, and without a significant increase in the level of the infused substance in the animal's bloodstream. However, sufficient receptors for direct or paracrine effects of some substances within a mammary gland may exist only during certain phases of the animal's physiology. For example, there appear to be a greater number of somatotropin-binding receptors in the bovine mammary gland during gestation than when the animals are not pregnant. Compare L'HORMONE PLACENTAIRE SOMATOMAMMOTROPE BOVINE (Chapter V) by Jean-Francois Beckers, Universite de Liege, Faculte de Medecine Veterinaire (1983) with Hormonal Control of Casein Synthesis and Organ Culture of the Bovine Lactating Mammary Gland, Gertler et al, 49 J. Dairy Res. 387 (1982) and Lactogenic Hormones: Binding Sites, Mammary Growth, Secretory Cell Differentiation, and Milk Biosynthesis in Ruminants, Akers, 68 J. Dairy Sci. 501 (1985).

In many embodiments of the invention, the substance having a mitogenic effect is a polypeptide growth factor. Certain classes of such growth factors preferred for use in this invention have molecular weights generally lower than about 65,000, even more typically lower than about 23,000 and, in the case of growth factors having a direct mitogenic effect as described hereinbefore, typically lower than about 10,000. Some non-polypeptide substances, e.g. ovarian and placental steroids and agonists thereof, can be suitably employed in some instances. In either case, the substance may be naturally occurring, synthesized to simulate a naturally occurring substance, or synthesized to provide a substance that is unlike any naturally occurring compound but nevertheless has such a mitogenic effect.

A preferred class of polypeptide growth factors that can be used are the epidermal growth factors (EGF's). Typically, these interact with receptors on mammary epithelial cells to stimulate proliferation of such cells. EGF's of various mammalian species have been sequenced and identified by their amino acid sequences and/or configurations dictated by internal cross-linking of cysteine residues through disulfide bonds. One such EGF is a well-characterized single-chain polypeptide of 53 amino acids which can be isolated from submaxillary (salivary) glands of adult male mice. Another form of EGF, human urogastrone, is synthesized in the duodenum and salivary glands and can be isolated from human urine. Urogastrone is 70% homologous (37 of 53 common amino acids) with mouse EGF and has three disulfide bonds in the same positions. Available data indicate that human urogastrone and human EGF are identical. Bovine EGF, which can be synthesized chemically or in a microorganism (e.g. bacteria such as *E. coli*) or eucaryotic cell culture by use of recombinant DNA, is believed to have an amino acid sequence essentially as follows: Asn-Phe-Leu-Lys-Lys-Cys-Phe-Pro-Glu-Tyr-Thr-Pro-Asn-Phe-Glu-Gly-Tyr-Cys-Leu-Asn-Gly-His-Val-Cys-Ile-Tyr-Phe-Gly-Ile-Ala-Asn-Leu-Phe-Ser-Cys-His-Cys-Pro-Ile-Gly-Tyr-Pro-Gly-Lys-Arg-Gly-Glu-Tyr-Ile-Asp-Phe-Asp-Gly-Trp-Asp-Pro-His. For more information on EGF's, see "Epidermal Growth Factor" by Carpenter et al, 48 Ann. Rev. Biochem. 193–216 (1979) and Gregory, 257 Nature 325–27 (1975), both incorporated here by reference.

It is known that the entire amino acid sequence of human or mouse EGF is not necessary for mitogenic activity. E.g., U.S. Pat. No. 3,917,824 issued Nov. 4, 1975 to Gamble et al discloses molecular variations shortened (e.g. by 2, 5 or 6 amino acids) at the carboxy terminus; U.S. Pat. No. 4,035,485 issued July 12, 1977 to Gregory et al discloses a molecular variation shortened by 7 amino acids; U.S. Pat. No. 3,948,875 issued Apr. 6, 1976 to Cohen discloses EGF derivatives lacking the C-terminal Leu-Arg residues; PCT Appln. WO 83/04030 by Banks et al discloses urogastrone analogs that differ in identity or location of one or more amino acids; and PCT Appln. WO 85/01284 by Komoriya et al discloses polypeptides having EGF-like activity based on the presence of a ten-amino acid sequence corresponding to that between $Cys_{20}$ and $Cys_{31}$ of natural EFG; each incorporated herein by reference. To the extent these or similar molecular variations of EGF, analogs thereof, or other compounds that interact with EGF (or functionally similar) receptors in the mammary gland following intramammary infusion and achieve objectives of this invention in substantial measure, they are equivalents of EGF's for purposes of this invention.

Various procedures for preparing an EGF are known. E.g., Japanese Patent Appln. 59/027858 (Nippon Shinyaku) discloses condensing protected 1–5 amino acid peptides to form a protected tripentacontapeptide which is oxidized, after being deprotected, to make an EGF; European Patent Appln. 128,733 by Lee et al published Dec. 19, 1984 and Patent Appln. WO 85/00369 by Bell published Jan. 31, 1985 disclose EGF preparations by expression of recombined DNA; British Patent 2,092,155 to Sugimoto discloses production of an EGF by multiplying hybridoma cells; and U.S. Pat. No. 4,528,186 issued July 9, 1985 to Nishimura et al discloses recovery of an EGF from human urine. These disclosures are incorporated by reference.

In other preferred embodiments, the growth factor can be selected from fetal EGF's such as the alpha-type transforming growth factors. See European Patent Applns. 105,014 by Sporn et al and 190,018 by Todaro et al (disclosures incorporated here by reference). Typically, these interact with receptors in the mammary gland to provide the desired mitogenic activity. Another class of the various polypeptides useful in this invention is illustrated by the viral protein analogs disclosed in European Patent Appln. 199,769 based on WO 86/02650 by Brown et al.

In other embodiments, the growth factor can be a polypeptide from the insulin family, an analog of such a polypeptide, or another substance that interacts with insulin-like growth factor (IGF) or functionally similar receptors in the mammary gland to provide a mitogenic effect on the parenchyma. Preferably, the IGF employed is an IGF-I ("somatomedin") or IGF-II. Similar results can generally be obtained using insulin or a precursor thereof (e.g. pro-insulin) although the amounts required are much greater than those of an IGF.

There is extensive literature on identities of these insulin family growth factors and methods for their production. For example, amino acid sequences for human IGF-I and -II and their production by expression of recombinant DNA in microbial hosts are described in European Patent Applns. 128,733 (supra) and 123,228 (Chiron Corp.) published Oct. 31, 1984. IGF-I analogs having valine in amino acid position 59 are described in European Patent Appln. 158,892 by Niwa et al published Oct. 23, 1985. More information on IGF's can be found in Rinderknecht et al, 73 Proc. Natl. Acad. Sci. U.S.A. 2365 (1976); Zapf et al, 19 Curr. Top. Cell. Reg. 257 (1981); and Wilson et al, 95 J. Endocrin. 59–64 (1982). Preparations of insulin and pro-insulin are described in Johnson, 219 Sci. 632–37 (1983) and European Patent Appln. 55,945 (Genentech) published July 14, 1982. The disclosures cited in this paragraph are incorporated here by reference.

In other preferred embodiments, the substance to be infused can be selected from one or a mixture of the various compounds in the arachidonic acid metabolic pathway and analogs thereof that have a mitogenic effect on mammary epithelial cells. These include the prostaglandins (such as those of the A to F series) and their analogs, e.g. [11α,13E,15S]-11,15-Dihydroxy-9-oxoprost-13-en-1-oic acid ($E_1$), [5Z,11α,13E,15S]-11,15-Dihydroxy-9-oxoprosta-5,13-dien-1-oic acid ($E_2$), [13E,15S]-15-Hydroxy-9-oxoprosta-10,13-dien-1-oic acid ($A_1$), [5Z,13E,15S]-15-Hydroxy-9-oxoprosta-5,10,13-trien-1-oic acid ($A_2$), [13E,15S]-15-Hydroxy-9-oxoprosta-8[12],13-dien-1-oic acid ($B_1$), [5Z,13E,15S]-15S]-15-Hydroxy-9-oxoprosta-5,8[12],13-trien-1-oic acid ($B_2$), [5Z,9α,13E,15S]9,15-Dihydroxy-11-oxoprosta-5,13-dien-1-oic acid ($D_2$), [9α,11α,13E,15S]-9,11,15-Trihydroxyprost-13-en-1-oic acid ($F_1α$), [5Z,9α,11α,13E,15S]-6,9-Epoxy-11,15-dihydroxyprosta-5,13-dien-1-oic acid ($I_2$), all available from Sigma Chemical Co., St. Louis, Mo., Lutalyse® prostaglandin ($F_2α$) available from The Upjohn Co., Kalamazoo, Mich. and cloprostenol. Precursors and metabolites of these substances (e.g. arachidonic acid and its metabolites) that are similarly active in effecting mammary cell mitosis can also be used, and those with greater activity and/or longer half life can be used in correspondingly lower doses. Many of these substances are described in Advances in Prostaglandin, Thromboxane, and Leukotriene Research, Vol. 14 (especially pp. 1–43, 73–129 and 263–307) edited by J. E. Pike and D. R. Morton, Jr., Raven Press, New York, N.Y. (1985), and Prostaglandins and the Arachidonic Acid Cascade, Norman A. Nelson, et al, 60 Chem. Eng. News, p. 30 et seq (Aug. 16, 1982), both incorporated here by reference.

In other embodiments, the growth factor can be one or a mixture of the mammary-derived or mesenchyme-derived growth factor (MDGF) polypeptides described by W. R. Kidwell et al in 260(9) J. Biol. Chem. 5745–52 (1985) and 46 Cancer Res. 933–39 (February 1986), the disclosures of which are incorporated here by reference. These MDGF's can be obtained by purification from milk or mammary tumors in accordance with procedures disclosed in those publications.

Substances that can be infused to achieve a paracrine mitogenic effect include placental lactogens, certain anterior pituitary hormones such as somatotropins, and other polypeptides having sufficiently similar chemical structure to provide essentially similar mitogenic effect(s) for purposes of this invention. Placental lactogens of specified mammalian species can be obtained by purification from their placental tissues. Bovine placental lactogen, which can be synthesized by use of recombinant DNA in microorganisms or cell cultures, has the amino acid sequence essentially as follows:

Ala-Glu-Asp-Tyr-Ala-Pro-Tyr-Cys-Lys-Asn-Gln-Pro-
-Gly-Asn-Cys-Arg--
-Ile-Pro-Leu-Gln-Ser-Leu-Phe-Glu-Arg-Ala-Thr-
Leu-Val-Ala-Ser-Asn-Asn-Tyr-Arg-Leu-Ala-Arg-
Glu-Met-Phe-Asn-Glu-Phe-Asn-Lys-Gln-Phe-Gly-
Glu-Gly-Lys-Asn-Phe-Thr-Ser-Lys-Val-Ile-Asn-
Ser-Cys-His-Thr-Glu-Phe-Met-Thr-Thr-Pro-Asn-
Asn-Lys-Glu-Ala-Ala-Ala-Asn-Thr-Glu-Asp-Glu-
Ala-Leu-Leu-Arg-Leu-Val-Ile-Ser-Leu-Leu-His-Ser-
Trp-Asp-Glu-Pro-Leu-His-Gln-Ala-Val-Thr-Glu-
Leu-Leu-His-Arg-Asn-Gly-Ala-Ser-Pro-Asp-Ile-
Leu-Ala-Arg-Ala-Lys-Glu-Ile-Glu-Asp-Lys-Thr-
Lys-Val-Leu-Leu-Glu-Gly-Val-Glu-Met-Ile-Gln-
Lys-Arg-Val-His-Pro-Gly-Glu-Lys-Lys-Asn-Glu-
Pro-Tyr-Pro-Val-Trp-Ser-Glu-Lys-Ser-Ser-Leu-
Thr-Ala-Asp-Asp-Glu-Asp-Val-Arg-Gln-Thr-Ala-
Phe-Tyr-Arg-Met-Phe-His-Cys-Leu-His-Arg-Asp-
Ser-Ser-Lys-Ile-Ser-Thr-Tyr-Ile-Asn-Leu-Leu-Lys-
Cys-Arg-Phe-Thr-Pro-Cys.

Further information about bovine placental lactogen, its production and biological activity can be found in U.S. patent application Ser. No. 092,116 by John C. Byatt et al filed concurrently with this application, now abandoned. Bovine, ovine, porcine, human and other somatotropins can be obtained by various published procedures including that described in European Patent Appln. 177,478 published Apr. 9, 1986 (see Examples 40–41).

As aforesaid, infusion of a substance having a mitogenic effect in accordance with this invention should be completed far enough in advance of parturition that the resulting mammary tissue has adequate opportunity to differentiate into milk-producing cells. For substances having a direct mitogenic effect, e.g. IGF's, EGF's, prostaglandins, MDGF's, TGF-$\alpha$'s, insulins and combinations thereof, such infusion is most advantageously completed prior to about the last 5 (preferably 10) days of the mammal's pregnancy. When the substance is one providing a paracrine mitogenic effect, e.g. a somatotropin, placental lactogen or a mixture thereof, its administration can usually be continued until about 5 days before parturition without significantly detracting from the desired effect, although such administration during about the last 10 days of pregnancy may not substantially enhance that effect.

The amounts of the mitogenic activity-providing substance required by the present invention are very small, indicating an unexpectedly high efficiency in their use. For substances having a direct mitogenic effect, useful units doses for infusion of a gland may be no more than about 100 micrograms, and smaller doses may be effective in some instances. Unit doses up to about 10 milligrams or more can usually be administered without interfering with the desired effects, but doses less than about 1 milligram are generally preferable for economic reasons. In the case of substances having a paracrine mitogenic effect, such unit doses can be as little as about 10 milligrams, and smaller doses can be effective in some cases. Unit doses of such substances up to about 200 milligrams or more can generally be used without intolerably diminishing the desired effect, but doses less than about 100 milligrams are usually economically preferred.

The most desirable doses, frequencies and numbers of infusions can be determined by routine experimentation. Commonly, spacing treatments over as long a period as possible tends to afford maximum results, provided sufficient time remains thereafter for differentiation of the new parenchyma cells before parturition. In many cases, from 1 to about 5 successive infusions provide good results. These can be suitably spaced by, e.g., from 1 to about 10 (preferably from 2 to about 5) days. The fact that substantial increases in parenchyma growth can be achieved in such short periods of time was quite unexpected and has considerable commercial significance. Satisfactory total doses, i.e., the sum of the successive infusions of an individual mammary gland during a gestation or puberty prior to gestation, are generally at least about 100 micrograms, typically less than about 50 milligrams, and often preferably less than about 5 milligrams of a substance providing a direct mitogenic effect. For a substance having a paracrine mitogenic effect, satisfactory total doses are generally at least about 100 milligrams and typically less than about 500 milligrams.

Other substances that furnish effects essentially similar to those afforded by any of the various mitogenic activity-providing substances mentioned herein can be likewise used in this invention, if desired. While the invention can be practiced using a single mitogenic activity-providing substance, combinations of such substances may be advantageous in some instances. In many embodiments, it is desirable to infuse a mitogenic activity-providing substance corresponding closely to a substance naturally occurring in the species to be treated, e.g. a bovine EGF, IGF, placental lactogen and/or somatotropin for treatment of cattle. However, substances corresponding to those naturally occurring in other species are commonly also suitable.

Normally, the method of this invention is carried out using a composition adapted for administration to a mammal by intramammary infusion and containing an amount, effective to enhance the growth of mammary parenchyma in said mammal, of a substance having a mitogenic effect on mammary epithelial cells in that mammal. Such compositions should be physiologically tolerable, preferably substantially non-irritating and essentially free of endotoxins. If desired, the mitogenic activity-providing substance can be infused as a solid which may be finely divided or compressed in an advantageous shape and size, e.g. for prolonged release in the teat cistern. In other embodiments, it is desirable to use a vehicle that is substantially liquid at the mammal's body temperature, and preferably also at the ambient temperatures of infusion. Whether the infused composition is solid or fluid, it is normally advantageous for it to include a vehicle that enhances diffusion of the mitogenic activity-providing substance through the mammary gland. In some, but not all cases, it is advantageous for the vehicle to be substantially water-soluble. In most cases, it is advantageous to use a vehicle in which the mitogenic activity-providing substance is substantially soluble.

The most desirable type and quantity of vehicle for infusion of the mitogenic activity-providing substance can be determined by routine experimentation. To illustrate, 1–10 ml of a liquid vehicle having a pH in the physiological range, e.g. a physiological saline solution, Freund's Incomplete Adjuvant or a vegetable (e.g. peanut or sesame) or mineral oil, is typically satisfactory. Emulsions of two or more of such vehicles are commonly advantageous. Appropriate stabilizers, e.g. mono- and/or disaccharides, sugar and alcohols or neutral amino acids, may be included if desired.

This invention also provides a process for preparing compositions useful for enhancing the growth of mammary parenchyma in a mammal. In a generic embodiment, such a process comprises combining (e.g. dispersing) a substance having a mitogenic effect on mammary epithelial cells in said mammal in a vehicle that enhances diffusion (and preferably prolongs release) of the substance through a mammary gland of said mammal, said composition being adapted by said combining for administration to the mammal by intramammary infusion.

The following descriptions of specific embodiments of the invention are illustrative only and do not imply any limitation on the scope of the invention. All animals in these examples were physiologically normal (as defined hereinbefore). All temperatures are in degrees Celsius. Parts and percentages are by weight except where otherwise indicated.

A. EPIDERMAL GROWTH FACTORS

EXAMPLES 1-2

12 pregnant, non-lactating, cross-bred beef cows within their last 40–80 days of gestation were housed in a free-stall facility, fed a ration of alfalfa hay and pelleted concentrate, and administered 10 ml of an excipient (Freund's Incomplete Adjuvant emulsified with an equal volume of 0.9% sterile saline) into each quarter-udder by intramammary infusion through the streak canal on days 1, 3, 5, 7 and 9 of this study. Infusions were carried out using a 3.2 centimeter long, approximately 12 gauge, blunt-tipped plastic teat infusion cannula obtained from Jorgensen Laboratories, Loveland, Colo. Because front and rear udder halves are not of equal size, treatment vs. control comparisons were made between laterally opposite quarters, i.e., front right vs. front left and rear right vs. rear left. Treatments were randomly assigned to right or left udder-halves, with the contralateral half serving as its control. In the treatment infusions, the excipient contained 25 micrograms of human EGF (hEGF) obtained from G. D. Searle & Co., Ltd., U.K. (6 animals) or mouse EGF (mEGF) obtained from Collaborative Research Corp., Lexington, Mass. (the other 6 animals). The hEGF had been prepared by Searle by expression of recombinant DNA and subsequently further purified by filtration on a 10,000 MW filter to a purity above 90% determined by HPLC. The mEGF was culture-grade, Catalog No. 40001, from mouse submaxillary glands, prepared by the method of Savage et al, 247 J. Biol. Chem. 7609 (1972) with a purity of 98% determined on SDS polyacrylamide gel.

Prior to treatment, each animal was teat-dipped for 3 consecutive days and each teat was pre-cleaned with 70% ethanol in water on the day of treatment. On day 14 the cows were sacrificed and their mammary glands excised. Each udder (milked out if necessary) was skinned, divided along the median suspensory ligament and then into front right, front left, rear right and rear left udder quarters. Each quarter-udder was ground, a representative 200 gm sample was homogenized with 4 times its volume of water, and the total homogenate volume of each was measured.

To determine dry weight of each quarter-udder, three 10 ml aliquots of a 1:5 diluted homogenate were placed in pre-weighed pans, dried overnight at 60° and then dried and weighed to a consistent value.

To determine dry fat-free tissue weight of each quarter-udder, three 5 ml aliquots of the undiluted homogenate were extracted by the method of Anderson, 41 J. Anim. Sci. 118 (1975) except that samples were placed in pre-weighed 25×150 mm glass centrifuge tubes and extracted overnight with 10 ml ethanol:ether (3:1), then centrifuged (5 min at 500 rpm) and the supernatant aspirated; an additional 10 ml aliquot of ethanol:ether was added for a second extraction; and the sample was dried under nitrogen until a consistent value was obtained.

DNA in each quarter-udder was determined by the method of Burton, 12B Methods in Enzymol. 163–66 (1968) using an assay solution of 15% trichloroacetic acid (TCA) in 2N HCl. In these determinations, aliquots of gland homogenate were diluted 1:5 with water and rehomogenized. Using triplicate 0.25 ml or 0.5 ml aliquots of these homogenates, each aliquot was mixed with 2 ml of the assay solution. After 30 min, the samples were centrifuged for 10 min at 3000 rpm and the resulting pellets were washed with 2 ml of a 10% solution of TCA in distilled water. After recentrifugation, the resulting pellets were disrupted in 2 ml of 0.5N perchloric acid and heated for 30 min at 70° to extract DNA. Samples were centrifuged and 1 ml of each resulting supernatant was placed in a 12×75 mm tube. After addition of 2 ml of a solution of 1.5 g diphenylamine and 1.5 ml H$_2$SO$_4$ in 100 ml glacial acetic acid (and 0.1 ml of 1.6% aqueous acetaldehyde per 20 ml reagent just prior to use), the sample were vortexed and incubated overnight at 27°. Calf thymus DNA was the standard.

Results are in Tables 1 and 2.

TABLE 1

Effects of Intramammary Infusion of hEGF on Quarter-Udders in Pregnant Beef Cows

| | Wet Weight, g | Dry Weight, g | Dry Fat-Free Weight, g | DNA, mg |
|---|---|---|---|---|
| A. Treatment Mean | 389.9 | 120.0 | 63.2 | 794.5 |
| B. Control Mean (Excipient only) | 357.3 | 111.4 | 58.3 | 710 |
| C. Mean Increase (A − B) | 32.6 | 8.6 | 4.9 | 84.5 |
| D. % Increase, (A − B)/B | 9.1 | 7.7 | 8.4 | 11.9 |
| E. Avg % Increase/Animal | 12.9 | 13.1 | 16.1 | 14.8 |
| F. Sig. Level of % Increase, p< | 0.01 | 0.09 | 0.16 | 0.06 |

TABLE 2

Effects of Intramammary Infusion of mEGF on Quarter-Udders in Pregnant Beef Cows

| | Wet Weight, g | Dry Weight, g | Dry Fat-Free Weight, g | DNA, mg |
|---|---|---|---|---|
| A. Treatment Mean | 419.6 | 150.2 | 69.6 | 905.1 |
| B. Control Mean (Excipient only) | 402.0 | 147.9 | 64.6 | 794.9 |

TABLE 2-continued

Effects of Intramammary Infusion of mEGF on Quarter-Udders in Pregnant Beef Cows

| | Wet Weight, g | Dry Weight, g | Dry Fat-Free Weight, g | DNA, mg |
|---|---|---|---|---|
| C. Mean Increase (A − B) | 17.6 | 2.3 | 5.0 | 110.2 |
| D. % Increase, (A − B)/B | 4.4 | 1.6 | 7.9 | 13.8 |
| E. Avg % Increase/Animal | 1.8 | 2.1 | 5.2 | 12.0 |
| F. Sig. Level of % Increase, p< | 0.22 | 0.40 | 0.19 | 0.05 |

As shown in Tables 1 and 2, quarter-udders infused with hEGF or mEGF were consistently heavier and contained more DNA than their laterally-opposite control quarters that received excipient only, and at generally high levels of statistical significance.

EXAMPLES 3–6

24 pregnant, non-lactating, cross-bred beef cows within their last 40–80 days of gestation were randomly divided into 4 treatment groups with 6 animals in each group. The effects of intramammary infusion of human EGF on quarter-udders in these animals were determined as described in Example 1 except that (A) as the excipient, the Freund's emulsion was used for Group 1 and an emulsion containing 60 parts sesame oil and 40 parts injectable grade 0.9% sterile saline containing 0.5% Tween-20 was used for Groups 2, 3 and 4 and (B) the amounts of hEGF included in each treatment infusion were 25 micrograms for Groups 1 and 2, 2.5 micrograms for Group 3, and 250 micrograms for Group 4. DNA determinations were made as in Examples 1–2 except that the initial triplicate 0.5 ml aliquots of homogenate were extracted with 2 ml of ethanol:ether (3:1) for 1 hour, centrifuged for 15 min at 3000 rpm, washed with 2 ml of 70% ethanol for 10 min, centrifuged at 3000 rpm for 15 min and aspirated of ethanol prior to mixing of each aliquot with the TCA solution. Results for Groups 1–4 are in Tables 3–6, respectively.

TABLE 3

Effects of Intramammary Infusion of a Total of 125 Micrograms of hEGF in Freund's Emulsion on Quarter-Udders in Pregnant Beef Cows (Group 1)

| | Wet Weight, g | Dry Weight, g | Dry Fat-Free Weight, g | DNA, mg |
|---|---|---|---|---|
| A. Treatment Mean | 364.9 | 107.2 | 60.3 | 723.0 |
| B. Control Mean (Excipient only) | 349.5 | 101.0 | 56.8 | 629.0 |
| C. Mean Increase (A − B) | 15.4 | 6.2 | 3.5 | 94.0 |
| D. % Increase, (A − B)/B | 4.4 | 6.1 | 6.2 | 14.9 |
| E. Avg % Increase/Animal | 8.1 | 10.3 | 8.3 | 23.0 |
| F. Sig. Level of % Increase, p< | 0.15 | 0.11 | 0.13 | 0.18 |

TABLE 4

Effects of Intramammary Infusion of a Total of 125 Micrograms of hEGF in Sesame Emulsion on Quarter-Udders in Pregnant Beef Cows (Group 2)

| | Wet Weight, g | Dry Weight, g | Dry Fat-Free Weight, g | DNA, mg |
|---|---|---|---|---|
| A. Treatment Mean | 370.2 | 122.1 | 71.0 | 995.0 |
| B. Control Mean (Excipient only) | 356.2 | 111.1 | 68.8 | 703.0 |
| C. Mean Increase (A − B) | 14.0 | 11.0 | 2.2 | 292.0 |
| D. % Increase, (A − B)/B | 3.9 | 9.9 | 3.2 | 41.5 |
| E. Avg % Increase/Animal | 10.4 | 20.2 | 15.9 | 70.0 |
| F. Sig. Level of % Increase, p< | 0.2 | 0.02 | 0.3 | 0.09 |

TABLE 5

Effects of Intramammary Infusion of a Total of 12.5 Micrograms of hEGF in Sesame Emulsion on Quarter-Udders in Pregnant Beef Cows (Group 3)

| | Wet Weight, g | Dry Weight, g | Dry Fat-Free Weight, g | DNA, mg |
|---|---|---|---|---|
| A. Treatment Mean | 397.8 | 132.4 | 79.4 | 867.6 |
| B. Control Mean (Excipient only) | 400.0 | 127.0 | 72.7 | 896.6 |
| C. Mean Increase (A − B) | (2.2) | 5.4 | 6.7 | (29.0) |
| D. % Increase, (A − B)/B | (0.5) | 4.2 | 9.2 | (3.3) |
| E. Avg % Increase/Animal | 0.6 | 7.8 | 16.3 | (2.2) |
| F. Sig. Level of % Increase, p< | — | 0.17 | 0.1 | — |

TABLE 6

Effects of Intramammary Infusion of a Total of 1.25 Milligrams of hEGF in Sesame Emulsion on Quarter-Udders in Pregnant Beef Cows (Group 4)

| | Wet Weight, g | Dry Weight, g | Dry Fat-Free Weight, g | DNA, mg |
|---|---|---|---|---|
| A. Treatment Mean | 391.9 | 131.5 | 81.7 | 733.2 |
| B. Control Mean (Excipient only) | 360.2 | 117.9 | 75.1 | 729.2 |
| C. Mean Increase (A − B) | 31.7 | 13.6 | 6.6 | 4.0 |
| D. % Increase, (A − B)/B | 8.8 | 11.6 | 8.8 | 0.5 |
| E. Avg % Increase/Animal | 9.9 | 12.2 | 11.9 | 1.6 |
| F. Sig. Level of % Increase, p< | 0.001 | 0.004 | 0.03 | — |

As shown in Tables 3–6, quarter-udders infused with hEGF were generally substantially heavier and contained more DNA than their laterally-opposite quarters that received excipient only.

EXAMPLES 7–8

24 pregnant, non-lactating, cross-bred beef cows within their last 40–80 days of gestation were randomly divided into 3 treatment groups with 8 animals in each group. The effects of intramammary infusion of human EGF on quarter-udders in these animals were determined as described in Examples 1–2 except that the amounts of hEGF included in each treatment infusion were 25 micrograms for Group 1, 250 micrograms for Group 2, and 2.5 micrograms for Group 3. Gland weights and DNA were determined as in Examples 1–2. Results with the low dose used for Group 3 were obscured by swellings of some glands. Results for Groups 1 and 2 are in Tables 7 and 8, respectively.

TABLE 7

Effects of Intramammary Infusion of a Total of 125 Micrograms of hEGF on Quarter-Udders in Pregnant Beef Cows (Group 1)

| | Wet Weight, g | Dry Weight, g | Dry Fat-Free Weight, g | DNA, mg |
|---|---|---|---|---|
| A. Treatment Mean | 363.0 | 113.0 | 52.8 | 396.9 |
| B. Control Mean (Excipient only) | 358.0 | 109.7 | 50.7 | 358.9 |
| C. Mean Increase (A − B) | 5.0 | 3.3 | 2.1 | 38.0 |
| D. % Increase, (A − B)/B | 1.5 | 3.0 | 4.1 | 10.6 |
| E. Sig. Level of % Increase, p< | 0.34 | 0.21 | 0.16 | 0.12 |

TABLE 8

Effects of Intramammary Infusion of a Total of 1.25 Milligrams of hEGF on Quarter-Udders in Pregnant Beef Cows (Group 2)

| | Wet Weight, g | Dry Weight, g | Dry Fat-Free Weight, g | DNA, mg |
|---|---|---|---|---|
| A. Treatment Mean | 392.5 | 122.0 | 63.8 | 344.0 |
| B. Control Mean (Excipient only) | 388.2 | 115.7 | 61.4 | 384.0 |
| C. Mean Increase (A − B) | 4.3 | 6.3 | 2.4 | (40.0) |
| D. % Increase, (A − B)/B | 1.1 | 5.3 | 3.9 | (10.4) |
| E. Sig. Level of % Increase, p< | 0.4 | 0.12 | 0.26 | — |

As shown in Tables 7–8, quarter-udders infused with hEGF were heavier than their laterally-opposite quarter-udders that received excipient only.

EXAMPLES 9–12

When dairy or beef heifers (either pregnant or non-pregnant) or pregnant dairy or beef cows within their last 25–60 days of gestation are infused using the procedures and dosages of Examples 3–6 with bovine EGF, results are essentially the same, i.e. substantial and statistically significant increases in the weights and DNA of the treated quarter-udders.

EXAMPLE 13

48 pregnant Holstein heifers within their last 40 days (approximately) of gestation were housed in a free-stall facility, fed a ration of alfalfa hay and pelleted concentrate, and administered 10 ml of an excipient into each quarter-udder by intramammary infusion through the streak canal every third day until parturition with the exception of one animal which was treated with human EGF as described in this Example only until 15 days before parturition. Infusions were carried out using a 3.2 centimeter long, approximately 12 gauge, blunt-tipped plastic teat infusion cannula obtained from Jorgensen Laboratories, Loveland, Colo. Animals were randomly assigned to each of the following 4 treatments (12 animals each): (A) 250 micrograms of human EGF obtained from G. D. Searle & Co., Ltd. (U.K.), solubilized (62.5 micrograms/ml) in sterile, injectable grade 0.9% saline containing 0.5% Tween-20 and then emulsified just prior to use in sterile sesame oil containing 5% Arlacel A mannide monooleate (3:2 oil: saline) with a final concentration of 25 micrograms/ml of hEGF in the excipient; (B) 250 micrograms of bovine IGF-I prepared as in Examples 14–16, purified and then solubilized and emulsified as just described for hEGF; (C) 50 milligrams of N-methionyl bovine somatotropin (BST) prepared as in Examples 40–41 and then diluted to 10 mg/ml in sterile sesame oil; and (D) a control using excipient (sterile sesame oil) alone. In each animal, all 4 quarter-udders received the same treatment. Each udder was sprayed with 70% ethanol and wiped dry prior to treatment and dipped with an iodine solution following treatment. At parturition, 4 animals from each treatment group were sacrificed and their mammary glands were removed for analysis. The other 8 animals from each treatment group were milked normally each a.m. and p.m. for the first 105 days of lactation.

During those 105 days, the animal treated with hEGF only until 15 days before parturition produced an average of 9.6 kg milk/day (34.8%) more than the average produced by the 8 control cows. On average, milk production by the cows treated until parturition did not exceed that of the control cows.

B. INSULIN-LIKE GROWTH FACTORS

EXAMPLES 14–16

24 pregnant, non-lactating, cross-bred beef cows within their last 40–80 days of gestation were housed in a free-stall facility, fed a ration of alfalfa hay and pelleted concentrate, and administered 10 ml of an excipient (a sesame oil emulsion of the kind used in Examples 4–6) into each half-udder by intramammary infusion through the streak canal on days 1, 3, 5, 7 and 9 of this study. The infusion technique, random assignment of half-udders to treatment or control, and treatment vs. control comparisons were as in Examples 1–2. In the treatment infusions, the excipient contained bovine insulin-like growth factor-I (bIGF-I) prepared by expression in E. coli (Prla Strain 079) of recombinant DNA coding for bIGF-I fused to the "lam" B cell wall protein signal sequence, secretion into the E. coli periplasmic space, and recovery/purification by conventional techniques including gel filtration, cation exchange and reverse-phase HPLC. This bIGF-I had the same amino acid sequence and secondary structure as the AMgen human IGF-I used in Example 20. In standard L6 myoblast assays, its activity was essentially the same (90–123%) as that of the Example 20 hIGF-I. The amounts of bIGF-I in each infusion were: Group 1–2.5 micrograms; Group 2–25 micrograms; Group 3–250 micrograms. Animals were prepared and infused, and their quarter-udder weights and DNA were determined as in Examples 3–6. Results for Group 1 are in Table 9.

TABLE 9

Effects of Intramammary Infusion of a Total of 12.5 Micrograms of bIGF-I on Quarter-Udders in Pregnant Beef Cows (Group 1)

| | Wet Weight, g | Dry Weight, g | Dry Fat-Free Weight, g | DNA, mg |
|---|---|---|---|---|
| A. Treatment Mean | 408.4 | 111.7 | 54.9 | 1307 |
| B. Control Mean (Excipient only) | 369.0 | 102.7 | 48.0 | 1219 |
| C. Mean In- | 39.4 | 9.0 | 6.9 | 88 |

TABLE 9-continued

Effects of Intramammary Infusion of a Total of 12.5 Micrograms of bIGF-I on Quarter-Udders in Pregnant Beef Cows (Group 1)

| | Wet Weight, g | Dry Weight, g | Dry Fat-Free Weight, g | DNA, mg |
|---|---|---|---|---|
| crease (A − B) | | | | |
| D. % Increase, (A − B)/B | 10.7 | 8.7 | 14.2 | 7.2 |
| E. Avg. % Increase/Animal | 11.0 | 8.8 | 16.0 | 12.5 |
| F. Sig. Level of % Increase, p< | 0.01 | 0.003 | 0.03 | 0.2 |

In this study, the two higher doses of bIGF-I (Groups 2-3) did not produce consistently greater growth of treatment quarters vs. control quarters. However, substantial growth of the non-infused quarters was observed. When the procedures described for Groups 1-3 were repeated, results were essentially the same. Pooling results from the original study and its replication, it was determined that both treatment and control quarter-udders had grown as follows:

TABLE 10

| Doses | Controls | Treatment | Combined |
|---|---|---|---|
| Medium vs. Low | +27%, p < 0.08 | +23.1%, p < 0.12 | +25% |
| High vs. Medium | +34.4%, p < 0.08 | +31.5%, p < 0.09 | +33% |
| High vs. Low | +71.3%, p < 0.007 | +62%, p < 0.01 | +67% |

The above increases in growth of the control quarter-udders occurred even though plasma levels of bIGF-I did not increase significantly during the study. Results were essentially the same when these tests were repeated using other pregnant, non-lactating beef cows grouped on the basis of essentially equal beginning udder volumes to remove that variable as much as possible from the test results.

EXAMPLES 17-19

When dairy or beef heifers (either pregnant or non-pregnant) or pregnant cows within their last 25-60 days of gestation are infused according to the procedure in Examples 14-16 with a total of 125 micrograms, 1.25 milligrams or 12.5 milligrams of bovine insulin-like growth factor-II purified essentially free from all other bovine peptides as in Example 1 of U.S. patent application Ser. No. 888,996 filed July 31, 1986 corresponding to European Patent Appln. 86870128.5, both incorporated herein by reference, the results are essentially the same as in Examples 14-16, i.e., substantial increases in the weights and DNA of the treated quarter-udders.

C. COMBINATIONS OF IGF'S AND EGF'S

EXAMPLE 20

30 mixed-breed sheep within their last 35-45 days of gestation were fed a ration of alfalfa hay and sheep chow and administered 2.5 ml of an excipient (a Freund's emulsion of the kind used in Examples 1-2 for 15 sheep; physiological (0.9%) saline solution for the other 15) into each half-udder by intramammary infusion through the streak canal on days 1, 3, 5, 7 and 9 of this study. Infusions were carried out using a 3.2 centimeter long, 16 gauge, blunt-tipped Teflon sheath from a C. R. Bard, Inc. A-cath cannula for placement of indwelling catheters. Udder halves in each animal were randomly assigned to treatment in which the excipient contained additionally 2.5 micrograms of mouse EGF of the kind used in Examples 1-2 and 2.5 micrograms of human IGF-I prepared by expression of recombinant DNA and sold by AMgen Biological Corp., Thousand Oaks, Calif. (Catalog No. 04111, Lot 407; over 90% pure as determined by HPLC). The other udder half in each animal was assigned to control in which the excipient only was infused. Prior to treatment, each animal was teat-dipped for 7 consecutive days and each teat was pre-cleaned with 70% ethanol in water on the day of treatment.

On day 13 the sheep were sacrificed and their mammary glands excised. Each udder (milked out if necessary) was skinned and divided along the median suspensory ligament into right and left udder halves. Each half-udder was homogenized with 4 times its weight of water, and the total homogenate volume of each was measured.

To determine dry weight of each half-udder, three 10 ml aliquots of a 1:5 diluted homogenate were placed in pre-weighed pans, dried overnight at 60° and then dried and weighed to a consistent value.

To determine dry fat-free tissue weight of each half-udder, three 5 ml aliquots of the undiluted homogenate were extracted by the method of Anderson, 41 J. Anim. Sci. 118 (1975) except that samples were placed in pre-weighed 25×150 mm glass centrifuge tubes and extracted overnight with 10 ml of ethanol:ether (3:1), then centrifuged (5 min at 500 rpm) and the supernatant aspirated; an additional 10 ml aliquot of ethanol:ether was added for a second extraction; and the sample was dried under nitrogen and weighed until a constant value was obtained.

DNA in each half-udder was determined by the method of Burton, Biochemistry 62315 (1956) using an assay solution of 15% trichloroacetic acid (TCA) in 2N HCl. In these determinations, aliquots of gland homogenate were thawed, diluted 1:5 with water and rehomogenized. Using triplicate 0.5 ml aliquots of these homogenates, each aliquot was mixed with 2 ml of the assay solution. After 30 min, the samples were centrifuged for 10 min at 3000 rpm and the resulting pellets were washed with 2 ml of a 10% solution of TCA in distilled water. After recentrifugation, the resulting pellets were disrupted in 2 ml of 0.5N perchloric acid and heated for 30 min at 70° to extract DNA. Samples were centrifuged and 1 ml of each resulting supernatant was placed in a 12×75 mm tube. After addition of 2 ml of a solution of 1.5 g diphenylamine and 1.5 ml $H_2SO_4$ in 100 ml glacial acetic acid (and 0.1 ml of 1.6% aqueous acetaldehyde per 20 ml reagent just prior to use), the samples were vortexed and incubated overnight at 20°. Calf thymus DNA was the standard.

Results are in Table 11.

TABLE 11

Effects of Intramammary Infusion of a Combination of mEGF and hIGF-I on Half-Udders in Pregnant Sheep

| | Wet Weight, g | Dry Weight, g | Dry Fat-Free Weight, g | DNA, mg |
|---|---|---|---|---|
| A. Treatment Mean | 277.3 | 73.6 | 75.2 | 1021.2 |
| B. Control Mean (Excipient only) | 264.7 | 66.2 | 56.4 | 849.5 |
| C. Mean Increase (A − B) | 12.5 | 7.4 | 18.8 | 171.7 |
| D. % Increase, | 4.7 | 11.0 | 33.0 | 20.2 |

TABLE 11-continued

Effects of Intramammary Infusion of a Combination of mEGF and hIGF-I on Half-Udders in Pregnant Sheep

| | Wet Weight, g | Dry Weight, g | Dry Fat-Free Weight, g | DNA, mg |
|---|---|---|---|---|
| (A − B)/B E. Sig. Level of Increase, p< | 0.016 | 0.03 | 0.001 | 0.002 |

The data in Table 11 show that DNA and wet, dry and dry fat-free weights of the half-udders treated in accordance with this invention were substantially increased relative to the untreated half-udders in the same animals, and at exceptionally high levels of statistical significance.

EXAMPLE 21

8 non-pregnant Holstein heifers about 18 months of age were tested for the effects of intramammary infusion of a combination of bovine IGF-I and human EGF according to the procedures used in Examples 14–16 with the exceptions that (A) the volume of excipient in each infusion was 2.5 ml, (B) each treatment infusion contained 6.25 micrograms of bIGF-I and 625 micrograms of hEGF of the kinds used in Examples 14–16 and 1–2, respectively, and (C) DNA's were not determined. Results are in Table 12.

TABLE 12

Effects of Intramammary Infusion of a Combination of hEGF and bIGF-I on Quarter-Udders in Holstein Heifers

| | Wet Weight, g | Dry Weight, g | Dry Fat-Free Weight, g |
|---|---|---|---|
| A. Treatment Mean | 205.1 | 93.2 | 10.7 |
| B. Control Mean (Excipient only) | 188.2 | 89.0 | 9.5 |
| C. Mean Increase (A − B) | 16.9 | 4.2 | 1.2 |
| D. % Increase (A − B/B) | 8.9 | 4.7 | 12.1 |
| E. Avg. % Increase/Animal | 11.3 | 7.7 | 18.8 |
| F. Sig. Level of Increase, p< | 0.06 | 0.2 | 0.09 |

The data in Table 12 show that the wet, dry and dry fat-free weights of Holstein heifer quarter-udders treated in accordance with this invention were substantially greater than their laterally-opposite quarter-udders that received excipient only, and at high levels of statistical significance.

EXAMPLE 22

The effects of intramammary infusion of a combination of bovine IGF-I and human EGF on 8 pregnant, non-lactating, cross-bred beef cows within their last 40–80 days of gestation were determined by the procedures described in Examples 14–16. Each treatment infusion contained 25 micrograms of hEGF of the kind used in Examples 1–2 and 250 micrograms of bIGF-I of the kind used in Examples 14–16. Results are in Table 13.

TABLE 13

Effects of Intramammary Infusion of a Combination of bIGF-I (a Total of 1.25 Milligrams) and hEGF (a Total of 125 Micrograms) on Quarter-Udders in Pregnant Beef Cattle

| | Wet Weight, g | Dry Weight, g | Dry Fat-Free Weight, g | DNA, mg |
|---|---|---|---|---|
| A. Treatment Mean | 496.1 | 156.4 | 72.0 | 1392 |
| B. Control Mean (Excipient only) | 474.0 | 144.0 | 60.7 | 1243 |
| C. Mean Increase (A − B) | 22.1 | 12.4 | 11.3 | 149 |
| D. % Increase, (A − B)/B | 4.7 | 8.6 | 18.7 | 12.0 |
| E. Avg. % Increase/Animal | 8.2 | 13.0 | 11.0 | 12.0 |
| F. Sig. Level of % Increase, p< | 0.1 | 0.03 | 0.08 | 0.15 |

As shown in Table 13, quarter-udders receiving the combination of bIGF-I and hEGF were consistently heavier and contained more DNA than their laterally-opposite control quarters, and at high levels of statistical significance.

EXAMPLES 23–24

18 pregnant Holstein heifers within their last 40–60 days of expected calving were housed in a free-stall facility, fed a ration of alfalfa hay and pelleted concentrate and administered 10 ml of an excipient (sterile sesame oil) into each quarter-udder by intramammary infusion through the steak canal every third day for the number of treatments shown below. The heifers in Groups 1 and 3 were treated no later than their fifth day before parturition; treatments of those in Groups 2 and 4 were continued into their last five days. Treatments containing a mitogenic substance were administered to both quarter-udders on one side of each animal. Excipient only was administered to both quarter-udders on the opposite side of that animal. All infusions were carried out with a Jorgensen Laboratories infusion canula of the kind used in Examples 1–2. Each teat was sprayed with 70% ethanol and wiped dry prior to treatment, and dipped with an iodine solution following treatment.

| Group | No. of Heifers | Mitogenic Substance In The Excipient | No. of Treatments Range | Avg. |
|---|---|---|---|---|
| 1 | 4 | hEGF & IFG-I* (0.25 mg each) | 10 | 10 |
| 2 | 5 | hEGF & IGF-I* (0.25 mg each) | 7–20 | 14 |
| 3 | 5 | BST** (50 mg) | 10–20 | 12 |
| 4 | 4 | BST** (50 mg) | 4–16 | 9 |

*Obtained as in Examples 1–2 and 14–16, respectively, solubilized (62.5 micrograms/ml of each) in sterile, injectable-grade 0.9% saline containing 0.5% Tween-20 and emulsified into the sterile sesame oil excipient (3:2 oil: saline) and 5% Arlacel A (Sigma Chemical Co., St. Louis, MO).
**Prepared as in Examples 40–41 and diluted to 10 mg/ml in the sesame oil excipient. See results in Examples 42–43.

These animals were milked normally each a.m. and p.m. for the first 30 days after parturition, with milk production recorded separately for each quarter-udder. On average, milk production by the half-udders that had been treated in Group 2 did not exceed that of their control half-udders.

TABLE 14

Effects of Intramammary Infusion of a Combination of hEGF and IGF-I on Quarter-Udders

TABLE 14-continued in Pregnant Heifers (Group 1)

| Average Milk Production, kg/day | | | |
|---|---|---|---|
| Treated Side (A) | Control Side (B) | % Increase, (A − B)/B | Sig. Level of Increase, p< |
| 10.0 | 9.0 | 11 | 0.14 |

As shown in Table 14, quarter-udders infused with a combination of hEGF and IGF-I no later than the fifth day before parturition produced, on average, substantially more milk than their laterally-opposite quarters that received excipient only.

D. PROSTAGLANDINS

EXAMPLES 25–28

24 pregnant, non-lactating, cross-bred beef cows in their last 45–105 days of gestation were housed in a free-stall facility, fed a ration of alfalfa hay and pelleted concentrate, and administered 5 ml of an excepient (MCT-Oil, a Mead Johnson Corp. medium chain triglyceride which is a lipid fraction of coconut oil consisting primarily of triglycerides of $C_8$ and $C_{10}$ fatty acids as follows: $C_8$-67%; $C_{10}$-23%; $<C_8$-6%; $>C_{10}$-4%) into each quarter-udder by intramammary infusion through the streak cannal on days 1, 3, 5, 7 and 9 of this study. The 48 front and rear udder halves were randomly divided into 4 groups, with one quarter of each udder half treated and its laterally opposite quarter-udder used as a control. In the treatment infusions, the excipient contained Prostaglandin (PG) $E_1$ or $E_2$ from Sigma Chemical Co., St. Louis, Mo. (Catalog Nos. 86F—0406 and —0404). The amounts of PG in each infusion were: Group 1—87.5 micrograms of $E_2$; Group 2—875 micrograms of $E_2$; Group 3—87.5 micrograms of $E_1$; Group 4—875 micrograms of $E_1$. Animals were prepared and infused as in Examples 23–24; the effects were determined as in Examples 1–2. Results for Groups 1–4 are in Tables 15–18, respectively.

TABLE 15

Effects of Intramammary Infusion of Prostaglandin $E_2$ (a Total of 0.4375 Milligrams) on Quarter-Udders in Pregnant Beef Cattle (Group 1)

| | Wet Weight, g | Dry Weight, g | Dry Fat-Free Weight, g | DNA, mg |
|---|---|---|---|---|
| A. Treatment Mean | 1966.9 | 525.5 | 351.8 | 5203 |
| B. Control Mean (Excipient only) | 1735.5 | 484.9 | 297.8 | 4724 |
| C. Mean Increase (A − B) | 231.4 | 40.6 | 54.0 | 479 |
| D. % Increase (A − B)/B | 13.3 | 8.3 | 18.1 | 10.1 |
| E. Sig. Level of % Increase, p< | 0.01 | 0.04 | 0.18 | 0.02 |

TABLE 16

Effects of Intramammary Infusion of Prostaglandin $E_2$ (a Total of 4.375 Milligrams) on Quarter-Udders in Pregnant Beef Cattle (Group 2)

| | Wet Weight, g | Dry Weight, g | Dry Fat-Free Weight, g | DNA, mg |
|---|---|---|---|---|
| A. Treatment Mean | 1030.8 | 312.7 | 194.5 | 3397 |
| B. Control Mean (Excipient only) | 742.0 | 219.0 | 144.3 | 2348 |
| C. Mean Increase (A − B) | 288.8 | 93.7 | 50.2 | 1049 |
| D. % Increase, (A − B)/B | 38.9 | 42.8 | 34.8 | 44.6 |
| E. Sig. Level of % Increase, p< | 0.0003 | 0.0001 | 0.004 | 0.001 |

TABLE 17

Effects of Intramammary Infusion of Prostaglandin $E_1$ (a Total of 0.4375 Milligrams) on Quarter-Udders in Pregnant Beef Cattle (Group 3)

| | Wet Weight, g | Dry Weight, g | Dry Fat-Free Weight, g | DNA, mg |
|---|---|---|---|---|
| A. Treatment Mean | 972.5 | 259.3 | 180.9 | 2881 |
| B. Control Mean (Excipient only) | 778.0 | 210.6 | 200.3 | 2284 |
| C. Mean Increase (A − B) | 194.5 | 48.7 | (19.4) | 597 |
| D. % Increase, (A − B)/B | 25.0 | 23.0 | (9.7) | 26 |
| E. Sig. Level of % Increase, p< | 0.002 | 0.002 | 0.58 | 0.07 |

TABLE 18

Effects of Intramammary Infusion of Prostaglandin $E_1$ (a Total of 4.375 Milligrams) on Quarter-Udders in Pregnant Beef Cattle (Group 4)

| | Wet Weight, g | Dry Weight, g | Dry Fat-Free Weight, g | DNA, mg |
|---|---|---|---|---|
| A. Treatment Mean | 1435.5 | 379.6 | 247.7 | 4218 |
| B. Control Mean (Excipient only) | 949.3 | 268.2 | 189.0 | 2792 |
| C. Mean Increase (A − B) | 486.2 | 111.4 | 58.7 | 1426 |
| D. % Increase, (A − B)/B | 51.2 | 41.5 | 31.0 | 51.1 |
| E. Sig. Level of % Increase, p< | 0.03 | 0.02 | 0.07 | 0.06 |

As shown in Tables 15–18, quarter-udders receiving the prostaglandins were consistently heavier and contained more DNA than their laterally-opposite control quarters that received excipient only, and at generally very high levels of statistical significance.

E. TRANSFORMING GROWTH FACTORS

EXAMPLES 29–32

When dairy or beef heifers (either pregnant or non-pregnant) or pregnant dairy or beef cows within their last 25–60 days of gestation are infused using the procedures and dosages of Examples 3–6 with human alpha-type transforming growth factor obtained from Bachem Inc. Fine Chemicals, Torrance, CA (Catalog #PGRO-30), results are essentially the same, i.e., substantial and statistically significant increases in the weights and DNA of the treated quarter-udders.

F. MAMMARY-DERIVED GROWTH FACTORS

EXAMPLES 33-36

When dairy or beef heifers (either pregnant or non-pregnant) or pregnant beef or dairy cows within their last 25-60 days of gestation are infused using the procedures and dosages of Examples 3-6 with $MDGF_1$ or $MDGF_2$ obtained by purification according to the aforecited Kidwell et al publications, results are essentially the same, i.e., substantial and statistically substantial increases in the weight and DNA of the treated quarter-udders.

G. INSULIN

EXAMPLES 37-39

When dairy or beef heifers (either pregnant or non-pregnant) or pregnant beef or dairy cows within their last 25-60 days of gestation are infused according to the procedures of Examples 3-6 with 25, 100 or 250 mg per infusion of bovine pancreas insulin from Sigma Chemical Co., St. Louis, MO (Catalog #I-5500; 24 IU/mg), results are similar, i.e., substantial and statistically significant increases in the weights and DNA of the treated quarter-udders.

H. SOMATOTROPINS

EXAMPLES 40-41

24 pregnant, non-lactating, cross-bred beef cows in their last 40-80 days of gestation were divided into 2 groups and tested for the effects of intramammary infusion using the procedures of Examples 3-6 except that (A) the volume of excipient in each infusion was 5 ml and (B) each treatment infusion contained a 1% zinc salt of an N-methionyl bovine somatotropin (BST) (Group 1—100 mg; Group 2—40 mg) prepared by expression of recombinant DNA and purified essentially as described in Example 1A of U.S. patent application Ser. No. 787,873 filed Oct. 16, 1985 based on European Patent Appln. 177,478 published Apr. 9, 1986, both incorporated here by reference. Results are in Tables 19-20.

TABLE 19

Effects of Intramammary Infusion of a Total of 500 Milligrams of BST on Quarter-Udders in Pregnant Beef Cows (Group 1)

|  | Wet Weight, g | Dry Weight, g | Dry Fat-Free Weight, g | DNA, mg |
|---|---|---|---|---|
| A. Treatment Mean | 790.1 | 207.6 | 146.7 | 2185 |
| B. Control Mean (Excipient only) | 736.6 | 190.6 | 141.5 | 2054 |
| C. Mean Increase (A − B) | 53.5 | 17.0 | 5.2 | 131 |
| D. % Increase, (A − B)/B | 7.3 | 8.9 | 3.6 | 6.4 |
| E. Avg. % Increase/Animal | 9.8 | 10.7 | 7.9 | 10.5 |
| F. Sig. Level of % Increase, p< | 0.004 | 0.03 | 0.18 | 0.3 |

TABLE 20

Effects of Intramammary Infusion of a Total of 200 Milligrams of BST on Quarter-Udders in Pregnant Beef Cows (Group 2)

|  | Wet Weight, g | Dry Weight, g | Dry Fat-Free Weight, g | DNA, mg |
|---|---|---|---|---|
| A. Treatment Mean | 396.9 | 96.4 | 49.5 | 1371 |
| B. Control Mean | 345.4 | 85.1 | 44.8 | 1299 |
| C. Mean Increase (A − B) | 51.5 | 11.3 | 4.7 | 72 |
| D. % Increase, (A − B)/B | 14.9 | 13.3 | 10.5 | 5.5 |
| E. Avg. % Increase/Animal | 13.4 | 10.7 | 7.8 | 15.8 |
| F. Sig. Level of % Increase, p< | 0.007 | 0.06 | 0.06 | 0.1 |

The data in Tables 19-20 show that the increases in DNA and wet, dry and dry fat-free weights of pregnant beef cow quarter-udders treated in accordance with this invention were substantially greater than those of their laterally-opposite quarter-udders that received excipient only, and that the differences between treatment and control increases are at high levels of statistical significance.

EXAMPLES 42-43

Shown in Table 21 are the milk production results obtained with the heifers of Group 3 in Examples 23-24. On average, milk production by the half-udders that had been treated in Group 4 of Examples 23-24 slightly exceeded (2%, p<0.4) that of their control half-udders.

TABLE 21

Effects of Intramammary Infusion of BST on Quarter-Udders in Pregnant Holstein Heifers (Group 4)

| Average Milk Production, kg/day | | % Increase, (A − B)/B | Sig. Level of Increase, p< |
|---|---|---|---|
| Treated Side (A) | Control Side (B) | | |
| 10.9 | 9.8 | 11 | 0.15 |

As shown in Table 21, quarter-udders infused with BST no later than the fifth day before parturition produced, on average, substantially more milk than their laterally-opposite quarters that received excipient only.

I. BOVINE PLACENTAL LACTOGENS

EXAMPLES 44-46

When dairy or beef heifers (either pregnant or non-pregnant) or pregnant beef or dairy cows within their last 40-80 days of gestation are infused according to the procedures of Examples 3-6 with a total of 0.25, 10 or 250 milligrams of natural bovine placental lactogen purified by the method of Byatt, 119 Endocrin. 1343-50 (1986), results are very similar, i.e., substantial and statistically significant increases in the weights and DNA of the treated quarter-udders.

Comparative Examples

Ovine Prolactins 16 pregnant, non-lactating, cross-bred beef cows in their last 30-105 days of gestation were divided into 2 groups and tested for the effects of intramammary infusion using the procedures of Examples 25-28 except that instead of a prostaglandin, each treatment infusion contained either 2 mg (Group 1) or 10 mg (Group 2) of ovine prolactin obtained from Sigma Chemical Co., St.

Louis, MO (Lot No. 26F-0076) in 10 ml of an emulsion of 0.9% saline containing 0.5% Tween-20 in sterile sesame oil containing 5% Arlacel A (3:2 oil: saline). Results are in Tables 22-23.

TABLE 22

Effects of Intramammary Infusion of Ovine Prolactin (a Total of 10 Milligrams) on Quarter-Udders in Pregnant Beef Cattle (Group 1)

|   | Wet Weight, g | Dry Weight, g | Dry Fat-Free Weight, g | DNA, mg |
|---|---|---|---|---|
| A. Treatment Mean | 895.3 | 262.7 | 137.8 | 2526 |
| B. Control Mean (Excipient only) | 889.9 | 257.9 | 136.6 | 2566 |
| C. Mean Increase (A − B) | 5.4 | 4.8 | 1.2 | (40) |
| D. % Increase (A − B)/B | .6 | 1.0 | .88 | (1.6) |
| E. Sig. Level of % Increase, $p<$ | 0.85 | 0.8 | 0.97 | — |

TABLE 23

Effects of Intramammary Infusion of Ovine Prolactin (Total dose of 50 milligrams) on Quarter-Udders in Pregnant Beef Cattle (Group 2)

|   | Wet Weight, g | Dry Weight, g | Dry Fat-Free Weight, g | DNA, mg |
|---|---|---|---|---|
| A. Treatment Mean | 1487.1 | 343.4 | 189.2 | 3672 |
| B. Control Mean (Excipient only) | 1308.5 | 349.0 | 184.5 | 3322 |
| C. Mean Increase (A − B) | 178.6 | (5.6) | 4.7 | 350 |
| D. % Increase (A − B)/B | 13.6 | (1.6) | 2.5 | 10.5 |
| E. Sig. Level of % Increase, $p<$ | 0.09 | — | 0.7 | 0.27 |

While the biological mechanisms of this invention are not fully understood, it is apparent that it can be used to provide, in accordance with conventionally recognized criteria, increases in mammary parenchyma and corresponding milk production capacity of treated animals that will persist through the animal's next lactation period, and in many cases through multiple subsequent lactations.

We claim:

1. A method for enhancing the proliferation of mammary parenchymal cells in a female ruminant wherein an amount effective to cause proliferation of mammary parenchyma cells, of a polypeptide growth factor having a molecular weight of less than 65,000 daltons and having a direct mitogenic effect on mammary epithelial cells in said ruminant is administered to the ruminant by intramammary infusion during gestation or between the onset of puberty and the ruminant's first gestation.

2. The method of claim 1 wherein the polypeptide growth factor has a molecular weight of less than 23,000 daltons.

3. The method of claim 2 wherein the polypeptide growth factor is an epidermal growth factor, an insulin family growth factor or a combination thereof.

4. The method of claim 3 wherein the polypeptide growth factor is an epidermal growth factor.

5. The method of claim 1 wherein the ruminant is a cow.

6. The method of claim 1 wherein the ruminant is a sheep.

7. The method of claim 1 wherein the ruminant is a goat.

8. A method for enhancing the proliferation of mammary parenchyma cells in a cow wherein an amount effective to cause proliferation of mammary parenchyma cells, of a polypeptide growth factor having a molecular weight of less than 65,000 daltons and having a direct mitogenic effect on mammary epithelial cells in the cow is administered to the cow by intramammary infusion during gestation or between the onset of puberty and the cow's first gestation.

9. The method of claim 8 wherein the polypeptide growth factor has a molecular weight of less than 23,000 daltons.

10. The method of claim 9 wherein the polypeptide growth factor is an epidermal growth factor, an insulin family growth factor, or a combination thereof.

11. The method of claim 10 wherein the polypeptide growth factor is an epidermal growth factor.

12. A method for enhancing the proliferation of mammary parenchyma cells in a goat wherein an amount effective to cause proliferation of mammary parenchyma cells, of a polypeptide growth factor having a molecular weight of less than 65,000 daltons and having a direct mitogenic effect on mammary epithelial cells in the goat is administered to the goat by intramammary infusion during gestation or between the onset of puberty and the goat's first gestation.

13. The method of claim 12 wherein the polypeptide growth factor has a molecular weight of less than 23,000 daltons.

14. The method of claim 13 wherein the polypeptide growth factor is an epidermal growth factor, an insulin family growth factor, or combination thereof.

15. The method of claim 14 wherein the polypeptide growth factor is an epidermal growth factor.

16. A method for enhancing the proliferation of mammary parenchyma cells in a sheep wherein an amount effective to cause proliferation of mammary parenchyma cells, of a polypeptide growth factor having a molecular weight of less than 65,000 daltons and having a direct mitogenic effect on mammary epithelial cells in the sheep is administered to the sheep by intramammary infusion during gestation or between about the onset of puberty and the sheep's first gestation.

17. The method of claim 16 wherein the polypeptide growth factor has a molecular weight of less than 23,000 daltons.

18. The method of claim 17 wherein the polypeptide growth factor is an epidermal growth factor, an insulin family growth factor, or combination thereof.

19. The method of claim 18 wherein the polypeptide growth factor is an epidermal growth factor.

* * * * *